(12) United States Patent
Hoyle, Jr.

(10) Patent No.: US 9,186,463 B2
(45) Date of Patent: Nov. 17, 2015

(54) DOSAGE CONTROL SYRINGE

(76) Inventor: John D. Hoyle, Jr., Rockford, MI (US)

( * ) Notice: Subject to any disclaimer, the term of this patent is extended or adjusted under 35 U.S.C. 154(b) by 371 days.

(21) Appl. No.: 13/702,874

(22) PCT Filed: Jun. 28, 2011

(86) PCT No.: PCT/US2011/042090
§ 371 (c)(1),
(2), (4) Date: Dec. 7, 2012

(87) PCT Pub. No.: WO2012/012127
PCT Pub. Date: Jan. 26, 2012

(65) Prior Publication Data
US 2013/0090603 A1    Apr. 11, 2013

Related U.S. Application Data

(60) Provisional application No. 61/359,892, filed on Jun. 30, 2010.

(51) Int. Cl.
*A61M 5/00* (2006.01)
*A61M 5/315* (2006.01)
*A61M 5/31* (2006.01)

(52) U.S. Cl.
CPC ......... *A61M 5/31526* (2013.01); *A61M 5/3129* (2013.01); *A61M 5/3158* (2013.01); *A61M 5/31555* (2013.01); *A61M 5/31563* (2013.01); *A61M 2005/3126* (2013.01)

(58) Field of Classification Search
CPC .................. A61M 2005/3126; A61M 5/31526; A61M 5/31555; A61M 5/31563
USPC .................................................. 604/207–210
See application file for complete search history.

(56) References Cited

U.S. PATENT DOCUMENTS

| | | |
|---|---|---|
| 2,369,304 A | 2/1945 | Lewis |
| 2,502,639 A | 4/1950 | Blake |
| 4,444,335 A | 4/1984 | Wood et al. |
| 4,563,178 A | 1/1986 | Santeramo |

(Continued)

FOREIGN PATENT DOCUMENTS

WO        9504563        2/1995

OTHER PUBLICATIONS

International Search Report and Written Opinion of the International Searching Authority from corresponding Patent Cooperation Treaty (PCT) Application No. PCT/US2011/042090, mailed Feb. 28, 2012.

*Primary Examiner* — Kevin C Sirmons
*Assistant Examiner* — Deanna K Hall
(74) *Attorney, Agent, or Firm* — Gardner, Linn, Burkhart & Flory, LLP

(57) ABSTRACT

A dosage control syringe includes a barrel, a plunger, an adjustable lock member supported along a guide (such as a track) that is disposed along or outside an outer wall of the syringe barrel, and a stop member coupled to the plunger or the lock member. The stop member is generally aligned between the adjustable lock member and a portion of the plunger so as to limit or preclude further movement of the plunger upon engagement of the stop member with both the lock member and the plunger. The plunger is stopped by the lock member, via the stop member, when the plunger has traveled a predetermined distance set by the lock member, the distance corresponding to a desired dosage of fluid from the syringe.

30 Claims, 5 Drawing Sheets

(56) References Cited

U.S. PATENT DOCUMENTS

| | | |
|---|---|---|
| 4,654,035 A | 3/1987 | Ando |
| RE32,974 E | 7/1989 | Porat et al. |
| 4,874,385 A | 10/1989 | Moran et al. |
| 4,950,163 A | 8/1990 | Zimble |
| 5,139,484 A | 8/1992 | Hazon et al. |
| 5,215,536 A | 6/1993 | Lampropoulos et al. |
| 5,328,486 A | 7/1994 | Woodruff |
| 5,344,409 A | 9/1994 | Ennis, III et al. |
| 5,380,295 A | 1/1995 | Vacca |
| 5,685,864 A | 11/1997 | Shanley et al. |
| 5,807,346 A | 9/1998 | Frezza |
| 6,283,941 B1 | 9/2001 | Schoenfeld et al. |
| 6,368,308 B1 | 4/2002 | Nerney |
| 6,413,241 B1 | 7/2002 | Slishman |
| 7,329,241 B2 | 2/2008 | Horvath et al. |
| 7,470,259 B2 * | 12/2008 | Hoyle, Jr. .............. 604/207 |
| 2001/0009990 A1 | 7/2001 | Hostettler |
| 2001/0051792 A1 | 12/2001 | Kirchhofer et al. |
| 2002/0010429 A1 | 1/2002 | Grogan, Jr. |
| 2002/0087121 A1 | 7/2002 | Slishman |
| 2009/0287161 A1 | 11/2009 | Traub et al. |

* cited by examiner

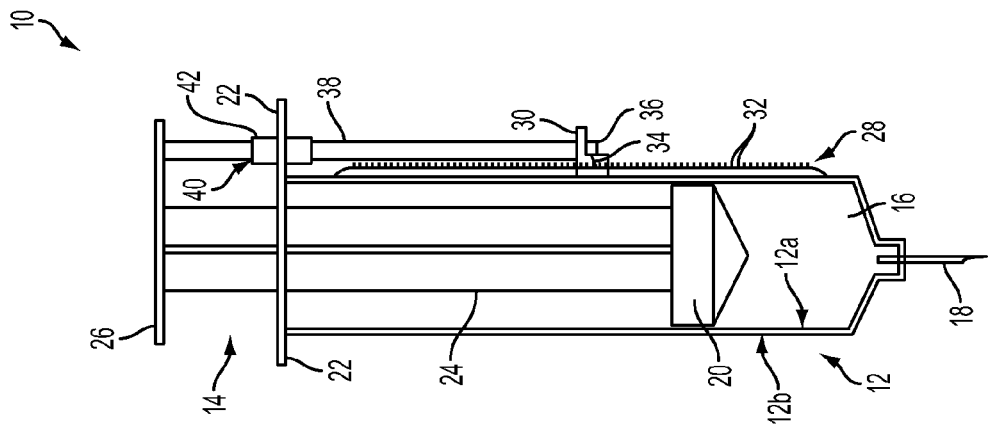
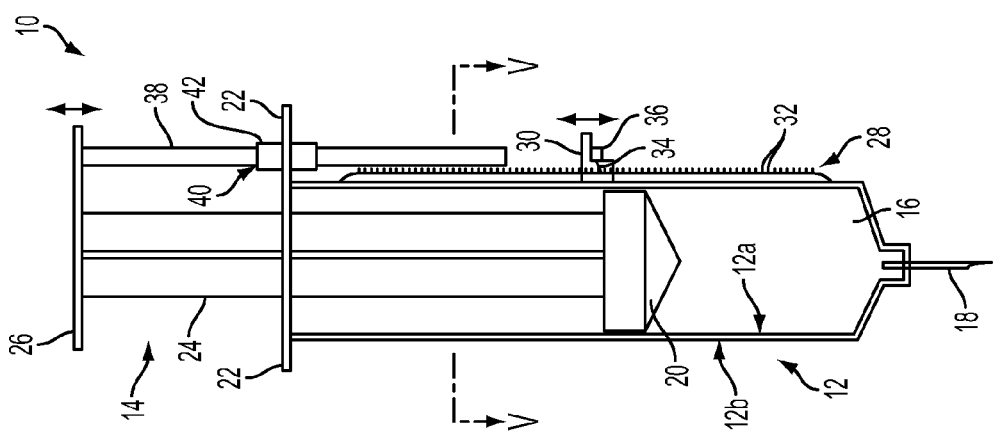

DOSAGE CONTROL SYRINGE

CROSS REFERENCE TO RELATED APPLICATIONS

The present application is both a §371 international and a continuation-in-part of International Patent Application No. PCT/US2011/042090, filed Jun. 28, 2011, which claims the benefit of U.S. provisional application Ser. No. 61/359,892, filed Jun. 30, 2010, both of which are hereby incorporated herein by reference in their entireties.

FIELD OF THE INVENTION

The present invention relates in general to the field of syringes, such as for use with hypodermic needles or for irrigating or administering fluids to small areas.

BACKGROUND OF THE INVENTION

Syringes are frequently used for administering drugs or other fluids to persons of widely-varying sizes, from small children to large adults, with correspondingly varied dosage requirements. Some syringes include indicia that are indicative of the fluid volume of the syringe, but measuring and administering proper dosage of a drug or fluid with such syringes typically requires calculations and accurate manipulation of the syringe to avoid overdosing or underdosing a patient. Administering the proper dosage for a given patient can be difficult since it can require carrying out a complex series of mathematical calculations. This process can be made more difficult by high stress and/or high workload environments, such as in emergency rooms, at accident scenes, or when dealing with critically ill patients, for example.

SUMMARY OF THE INVENTION

The present invention provides a dosage control syringe including an adjustable lock member that can be preset in a fixed location along a track or guide on the syringe. The invention may be particularly well-suited for use in high stress and/or high workload environments in which syringes are preloaded with fluid, such as liquid medication, when only a portion of the fluid in the syringe is to be administered to a patient. The syringe includes a barrel and a plunger, and a stop member that moves with the plunger or the adjustable lock member, and engages the other of the plunger or lock member to limit the travel of the plunger. The adjustable lock member is positioned along a track or guide that is disposed along or spaced from the outside of the syringe barrel. The lock member can be locked in a fixed location corresponding to a desired dosage, so that the lock member limits or prevents the plunger from being pushed too far, and thus limits or prevents administering an overdose of the fluid. Thus, the dosage control syringe can be preset for a desired dosage and the dosage may be subsequently administered without visual reference to the syringe or monitoring the position of the plunger along the syringe barrel, because the plunger will be stopped by the lock member, via the stop member, once the preset dosage is reached.

According to one form of the present invention, a dosage control syringe includes a barrel, a plunger, an elongate track or guide, and an adjustable lock member disposed along the track or guide. The barrel includes a longitudinal axis, an outer surface, and an inner surface. The inner surface of the barrel defines a fluid chamber, with both the outer and inner surfaces of the barrel spaced outwardly from the longitudinal axis. The plunger includes a first or lower end portion including a sealing member disposed in the fluid chamber of the barrel. The sealing member slidably and sealingly engages the inner surface of the barrel as the plunger travels along the barrel. A second or upper end portion of the plunger includes a flange extending outwardly away from the longitudinal axis of the barrel. The elongate track or guide is disposed outboard of the outer surface of the barrel, and is generally parallel to the longitudinal axis of the barrel. A stop member is disposed along or outboard of the barrel and aligned generally parallel with the longitudinal axis. The stop member is coupled to one of the adjustable lock member and the plunger flange, and is aligned so that it can selectively contact the other of the adjustable lock member and the plunger flange. When the plunger is moved sufficiently so that the stop member contacts the other of the adjustable lock member and the plunger flange, further movement of the plunger relative to the barrel is substantially precluded.

In one aspect, the adjustable lock member may be set between a locking configuration in which the lock member lockably engages the elongate guide, and a movable configuration in which the lock member is movable along the elongate guide.

In another aspect, the elongate track or guide is established along the outer surface of the barrel.

In a further aspect, the elongate guide is a track on which the adjustable lock member is received. Optionally, the stop member is a tubular member that also receives the track, such as in a telescoping manner. Optionally, the track includes a plurality of ratchet teeth and the lock member includes at least one tooth-engaging projection, the projection being operable to selectively engage at least one of the ratchet teeth to affix the position of the lock member along the elongate track, and the tooth-engaging projection further being operable to selectively disengage the ratchet teeth so that the lock member is movable along the elongate track. Optionally, the adjustable lock member includes a trigger release that can be actuated to disengage the tooth-engaging projection from the ratchet teeth of the track.

In yet another aspect, the stop member is coupled to the adjustable lock member and is configured to be engaged by an upper surface of the plunger flange when the plunger is withdrawn a distance from the barrel, the distance corresponding to a preselected volume of the fluid chamber.

In still another aspect, the barrel is a double-wall barrel having an outer wall and an inner wall. The outer wall is spaced outwardly from the inner wall and includes the outer surface of the barrel, while the inner wall includes the inner surface of the barrel and defines the fluid chamber. Optionally, the outer wall surrounds the entirety of the inner wall, or it may surround about one half of the inner wall, or it may surround less than half of the inner wall.

In yet another aspect, the track or guide is established along the outer surface of the inner wall of the double-wall barrel, and the outer wall includes a slot for receiving the guide and/or the adjustable lock member.

In a further aspect, the outer wall of the barrel includes indicia indicative of dosage. Optionally, the indicia is generally aligned with the elongate track or guide. The adjustable lock member may have a pointer or other indicator that aligns with the indicia to provide a clear indication of dosage corresponding to the position of the lock member.

In a still further aspect, the syringe barrel has a flange that extends generally perpendicular to the barrel's longitudinal axis from the open end of the barrel. The flange includes a through-hole for movably receiving the stop member of the plunger, so that when the stop member moves with the plunger (or when the stop member moves with the adjustable lock member), the stop member moves through the barrel flange through-hole as the plunger moves along the barrel (or as the adjustable lock member moves along the guide or track).

Thus, the dosage control syringe of the present invention provides a pre-settable dosing device that limits the travel of the syringe plunger so that only a desired quantity of medication or other fluid is dispensed from the syringe upon pressing the plunger. The syringe permits accurate dosing without visually monitoring the syringe during administration of the medication or other fluid contained therein.

These and other objects, advantages, purposes, and features of the present invention will become apparent upon review of the following specification in conjunction with the drawings.

BRIEF DESCRIPTION OF THE DRAWINGS

FIG. 1 is a side elevation of a dosage control syringe in accordance with the present invention, including a plunger that is partially withdrawn from the syringe barrel;

FIG. 2 is a side elevation of the dosage control syringe of FIG. 1, in which the plunger's travel is limited by the engagement of the stop member with the adjustable lock member;

DESCRIPTION OF THE PREFERRED EMBODIMENTS

Figure 4:
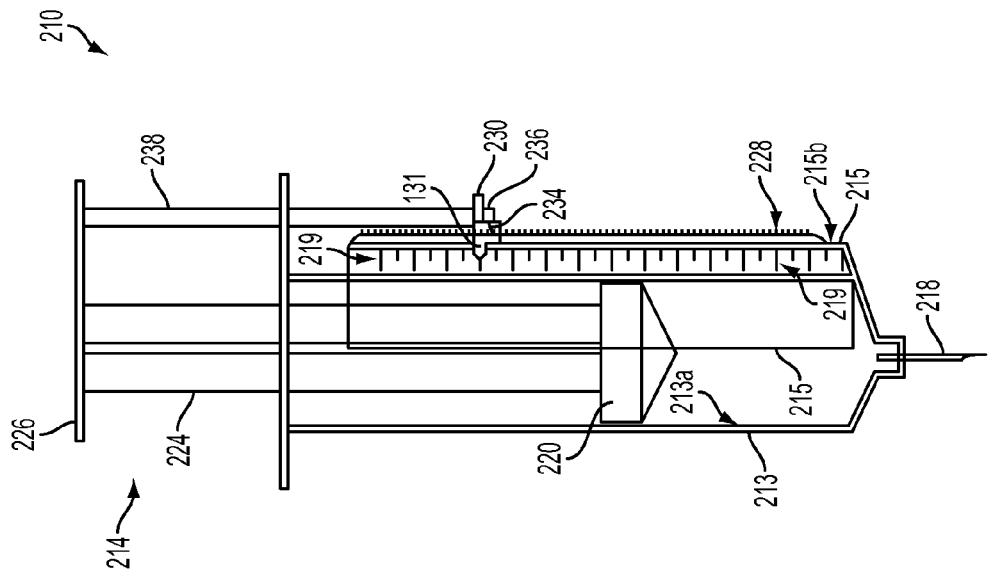
FIG. 4 is a side elevation of a dosage control syringe having a double wall around half of its circumference.

The present invention is directed to a syringe, and more specifically, to a syringe with a movable or adjustable dosage limiter that allows a user, such as a medical professional or a laboratory technician, to administer a pre-set dosage of fluid from the syringe. As will be more fully described below, the syringe may include a lock member that is movably disposed along a guide, such as an elongate track, that is disposed along or spaced from an outer surface of the syringe. In one embodiment, the lock member is movable along the guide or track, and is engaged or contacted by a stop member that is attached to a portion of a plunger. Optionally, the stop member may be attached to the lock member, and selectively engages the plunger. By adjusting the position of the lock member along the guide or track, a user may control the distance or extent to which the plunger may be pushed or urged along the barrel of the syringe to expel medication or other fluid from the fluid chamber of the syringe.

Referring now to FIGS. 1 and 2, a dosage control syringe 10 includes a barrel 12 and a plunger 14. Barrel 12 includes an inner surface 12a and an outer surface 12b, the inner surface 12a defining a fluid chamber 16. Barrel 12 further includes a flange or "ears" 22 at its open upper end. Barrel 12 supports a hypodermic needle 18 at the barrel's lower end. Barrel 12 may include indicia, such as volumetric gradations or weight-indicative indicia (not shown in FIGS. 1 and 2), to assist a user, such as a medical professional, in selecting proper dosage. Fluid chamber 16 receives plunger 14, which includes a sealing portion 20 at the lower end of a shaft 24, and a plunger flange 26 at the shaft's upper end. It should be understood that references to "upper" and "lower" throughout this specification are only used in the context of the relative positions in the drawings, and are not intended to be limiting in any way.

Figure 5:
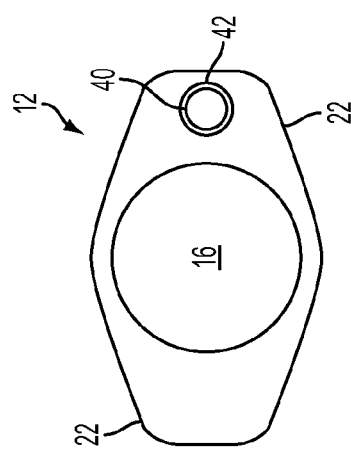
FIG. 5 is a top sectional view taken along section line V-V of FIG. 1.

Disposed along outer surface 12b of barrel 12 is a guide or guide member in the form of an elongate track 28 that movably supports an adjustable lock member 30. Elongate track 28 is parallel to the longitudinal axis of barrel 12, and extends radially from outer surface 12b of barrel 12. As best seen in FIG. 5, elongate track 28 may be generally T-shaped in cross section, while adjustable lock member 30 is generally C-shaped (as viewed from above, e.g., FIG. 5) so that lock member 30 is movably retained along track 28. It will be appreciated that elongate track 28 is merely exemplary of different types of guides or guide members capable of movably supporting an adjustable lock member. Other suitable guides or guide members may include, for example, a slot with elongated side edges that engage an I-shaped lock member, other shapes (i.e. non T-shapes) of elongate tracks, or the like, without departing from the spirit and scope of the present invention.

Elongate track 28 includes a plurality of teeth or ribs 32 (FIGS. 1 and 2) that are engaged by a tooth-engaging projection 34 of adjustable lock member 30. In its normal relaxed state or configuration, tooth-engaging projection 34 lockably engages one or more of teeth 32 along track 28. Optionally, the teeth or ribs 32 may be spaced apart from one another by a predetermined distance that corresponds to an incremental change in volume of fluid chamber 16, such as 0.1 mL per tooth 32, for example. In this manner, a user can detect volumetric changes by touch (i.e. by sensing the ratcheting movement of adjustable lock member 30) as well as by visual reference and audible reference (i.e. listening for individual "click" sounds associated with ratcheting). Adjustable lock member 30 includes a trigger release 36 that can be squeezed or depressed to move tooth-engaging projection 34 to a disengaging configuration, so that adjustable lock member 30 may be moved in either direction along track 28 and locked in a position corresponding to an appropriate dosage, such as by aligning the lock member with indicia on the barrel 12.

Optionally, adjustable lock member 30 may be slid or moved upwardly along elongate track 28 (as viewed in FIGS. 1 and 2), with tooth-engaging projection 34 ratcheting or sliding along teeth 32, without actuating trigger release 36. However, adjustable lock member 30 cannot be moved downwardly without first moving tooth-engaging projection 34 to its disengaging configuration by depressing trigger release 36. Therefore, lock member 30 may be readily slid from a lower position along track 28 (corresponding to a larger dose)

to a higher position along track 28 (corresponding to a smaller dose) by urging lock member 30 to ratchet upwardly along track 28, but lock member 30 cannot be moved to a lower position along track 28 (corresponding to a larger dose) without first actuating trigger release 36. Thus, adjustable lock member 30 and elongate track 28 may operate or interact in a similar manner as releasable or reusable "zip ties" that are commercially available from numerous suppliers and used for bundling wires and the like.

Figure 6:
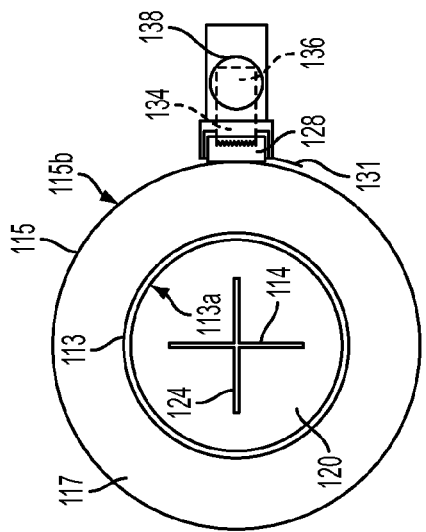
FIG. 6 is a top plan view of the barrel of the syringe of FIG. 1.

Plunger 14 supports a stop member 38 that extends or projects downwardly from plunger flange 26 (as viewed in FIGS. 1 and 2), and is parallel to plunger shaft 24 and the longitudinal axis of barrel 12. Stop member 38 is positioned in close proximity to track 28 and generally aligned with adjustable lock member 30. Stop member 38 may be in sliding contact with track 28, or may be spaced from the track. Stop member 38 is supported and guided or maintained in alignment with lock member 30 by barrel flange 22, which includes a through-hole 40 (FIG. 6) that is sized and shaped to receive stop member 38 and to allow the stop member to pass through hole 40. In the illustrated embodiment, stop member 38 is circular in cross section and through-hole 40 is correspondingly circular in shape, although it will be appreciated that substantially any cross section and corresponding hole size and shape may be used. Adjustable lock member 30 includes a generally flat surface that is contacted by stop member 38 (FIG. 2), although the portion of lock member 30 that is contacted by stop member 38 may be concave or cup-shaped, or larger in size, to limit or prevent the tip of stop member 38 from slipping off of the lock member 30, such as when excessive loads are applied to plunger 14.

Optionally, and as shown in FIGS. 1 and 2, flange 22 includes a support tube 42 that defines hole 40, and is axially aligned with stop member 38. Support tube 42 has an inner diameter or shape that generally corresponds to the outer diameter or shape of stop member 38, so that the support tube 42 limits or prevents buckling or flexing of the stop member when the stop member is placed under compressive axial loads. Thus, support tube 42 reduces the likelihood that a user would depress flange 26 of plunger 14 with sufficient force to cause the plunger to move a greater distance (corresponding to a higher dosage) than indicated by the position of lock member 30.

Accordingly, syringe 10 may be set for a desired dosage by moving adjustable lock member 30 along track 28 (actuating trigger release 36 as necessary), grasped with one or more fingers positioned below the ears or flange 22 of barrel 12 and the thumb positioned above the plunger flange 26, for example, and squeezed to urge the plunger 14 downwardly relative to barrel 12. The downward motion of sealing portion 20 of plunger 14 expunges fluid from fluid chamber 16 through needle 18 until stop member 38 contacts adjustable lock member 30, which limits or prevents further downward movement of plunger 14. Thus, the amount or dose of fluid dispensed from fluid chamber 16 is set or limited by the position of adjustable lock member 30 along track 28.

Figure 3:
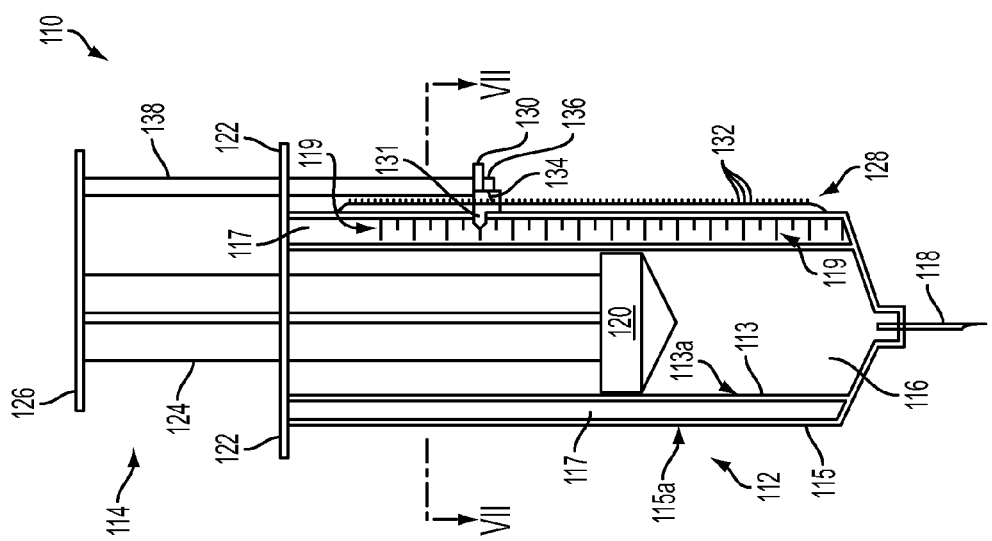
FIG. 3 is a side elevation of another dosage control syringe having a double wall around its entire circumference.
Figure 7:
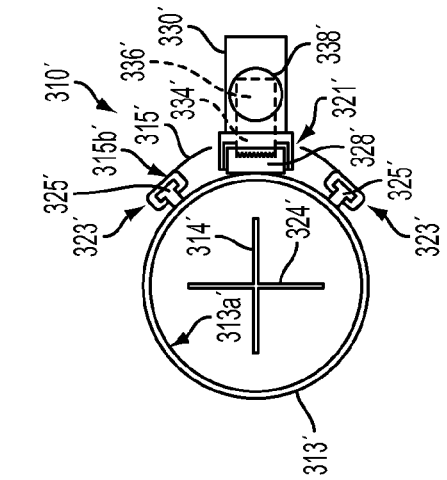
FIG. 7 is a sectional view taken along section line VII-VII of FIG. 3.

Another dosage control syringe 110 operates in a substantially similar manner as described above, but includes a double-wall barrel 112 having an inner wall 113 and an outer wall 115 disposed around the entire circumference of inner wall 113 (FIGS. 3 and 7). Inner wall 113 includes an inner surface 113a defining a fluid chamber 116 in substantially the same manner that inner surface 12a of barrel 12 defines fluid chamber 16 for syringe 10. Outer wall 115 includes an outer surface 115b along which a track 128 is supported. Outer wall 115 is spaced outboard of inner wall 113, with an annular open area 117 defined between the inner and outer walls.

Outer surface 115b of outer wall 115 may provide the benefit of increased size, compared to the surfaces of inner wall 113, on which to place indicia 119 (FIG. 3). This may also provide improved visual reference to the position of an adjustable lock member 130 relative to the indicia 119, due to the close proximity of the indicia 119 on outer wall 115 to the lock member 130.

Indicia 119 provides a guide or visual dosage indication with which to align an adjustable lock member 130 on track 128. For example, and as shown, indicia 119 may include volumetric or other types of markings (such as corresponding to patient weight, for example). Other types of indicia may include color-coding or a collar attached to the adjustable lock member and extending around the syringe barrel. Optionally, adjustable lock member 130 includes a pointer or indicator portion 131 that aligns with or points to indicia 119, and moves along the indicia as lock member 130 is moved, to provide the user with a clear visual indication of the dosage corresponding to the position of the lock member 130. It is further envisioned that other types of indicia could be used to aid users such as medical personnel to quickly and easy view, set, and confirm the proper dosage setting of adjustable lock member 130. For example, the adjustable lock member may have a viewing window (e.g., instead of a pointer) that aligns with indicia 119.

A barrel flange 122 is sized to extend beyond the diameter of outer wall 115, on which track 128 is supported, and includes a through-hole (similar to through-hole 40 of syringe 10) for receiving and supporting a stop member 138 in alignment with the adjustable lock member 130. Barrel flange 122 can optionally include a support tube to guide and support stop member 138, similar to barrel flange 22, described above. Various other components of syringe 110 are substantially similar to components of syringe 10 and are given like numerals by the addition of 100, such that the components of syringe 110 may be understood with reference to the above discussion of syringe 10.

Optionally, it will be appreciated that at least some of the benefits of a double-wall barrel may be achieved with an outer wall that surrounds less than the entirety of an inner wall. For example, and with reference to FIG. 4, another dosage control syringe 210 includes an inner wall 213 with an inner surface 213a defining a fluid chamber 216, and an outer wall 215 surrounding approximately one half of the circumference of inner wall 213. Outer wall 215 supports a track 228 on which an adjustable stop member 230 is movably supported, and provides a greater diameter than inner wall 213 on which to place indicia 219. Outer wall 215 may be formed unitarily with inner wall 213, or may be attached to inner wall 213 such as in a manner described below with reference to FIG. 8, in which a dosage control syringe 210' includes an inner wall 213' supporting a track 228', and a half outer wall 215' defining an elongate slot 221' that permits an adjustable lock member 230' to slide along track 228', which is aligned with slot 221'.

Figure 8:
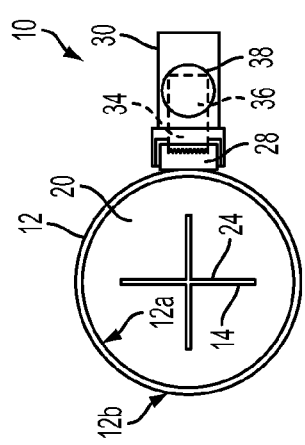
FIG. 8 is a sectional view of another syringe having a double wall around half of its circumference.

Syringe 210' has an outer wall 215' including a pair of C-shaped couplers 223' at opposed ends thereof, and arranged on either side of inner wall 213' (FIG. 8). A pair of corresponding T-shaped elongate projections 225' extend from opposite sides of inner wall 213', for receiving C-shaped couplers 223' of outer wall 215'. Accordingly, outer wall 215' may be slid into engagement with inner wall 213' by sliding C-shaped couplers 223' over and along T-shaped projections 225' or, optionally, C-shaped couplers 223' may be snapped over T-shaped projections 225'. It will be appreciated that various other methods or devices may be used for attaching a partial outer wall to an inner wall, without departing from the spirit and scope of the present invention.

Figure 9:
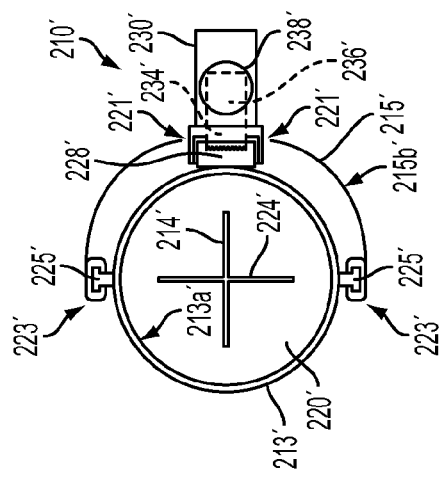
FIG. 9 is a sectional view of a syringe similar to that of FIG. 8, and having a double wall around one quarter of its circumference.

Optionally, a syringe 310' having an outer wall 315' that surrounds only about one-quarter of an inner wall 313' may still provide substantial benefits of an outer wall, without fully surrounding the inner wall 313' (FIG. 9). Like the syringe 110 of FIGS. 3 and 7, various other components of syringes 210, 210', and 310' that are substantially similar are given like numerals by the addition of 200, 200', or 300', respectively, such that the components of the syringes may be understood with reference to the earlier discussion(s) of one or more of syringes 10, 110, 210, and 210'.

Figure 10:
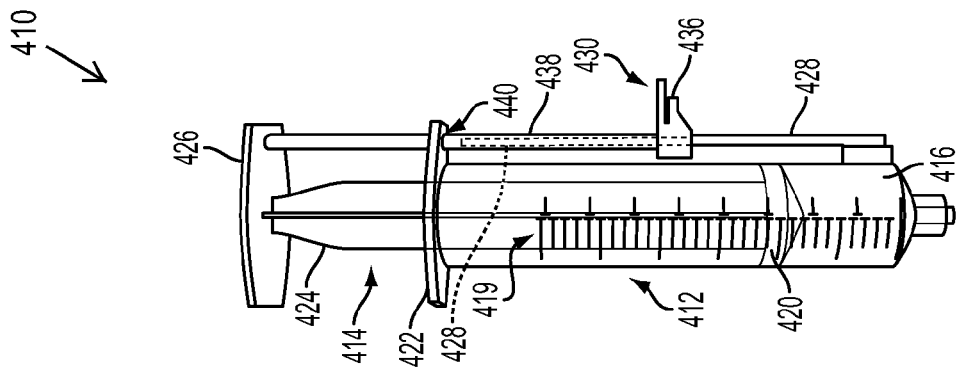
FIG. 10 is a side perspective view of another dosage control syringe, having its plunger mostly extracted and its stop member and adjustable lock member positioned according to a relatively larger dose.
Figure 11:
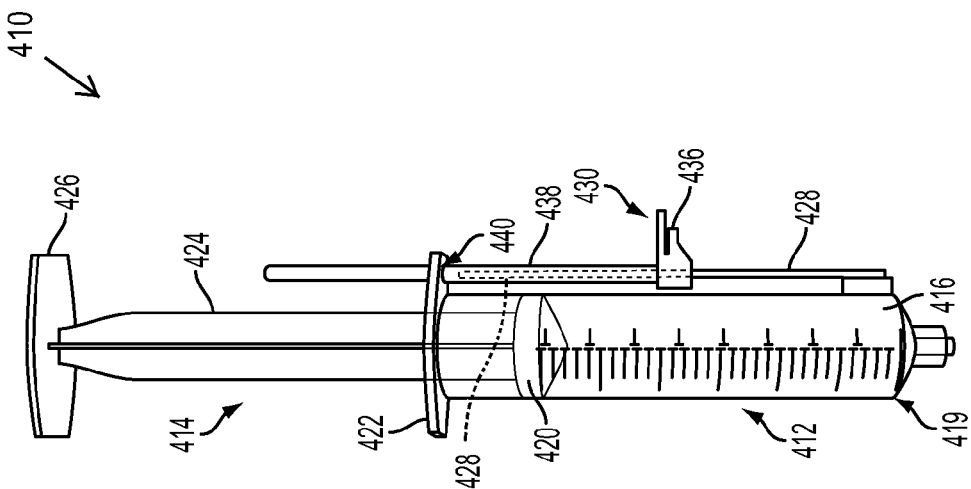
FIG. 11 is another side perspective view of the syringe of FIG. 10, having its plunger fully extracted and its stop member and adjustable lock member positioned according to a relatively smaller dose.
Figure 12:
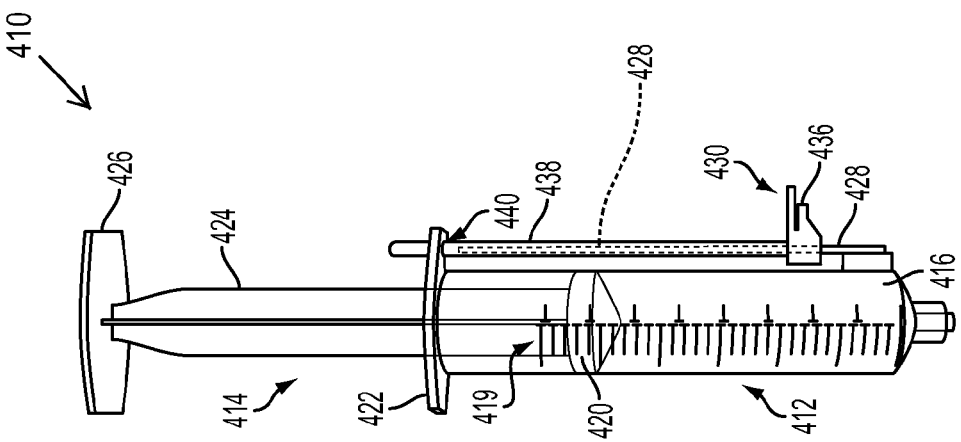
FIG. 12 is another side perspective view of the syringe of FIG. 11, having its plunger pushed down so that it is contacted and stopped by the stop member.

Another dosage control syringe 410, similar to syringe 10 described above, includes a barrel 412 and plunger 414 (FIGS. 10-12). Unlike syringes 10, 110, 210, 210', and 310', however, syringe 410 has a stop member 438 that extends or projects upwardly (as viewed in the drawings) from an adjustable lock member 430, which is repositionable and lockable along an elongate guide in the form of a track 428. Track 428 and adjustable lock member 430 may be substantially similar or identical to track 28 and adjustable lock member 30 of syringe 10, described above. In the illustrated embodiment of FIGS. 10-12, stop member 438 is a tubular member having a hollow central portion that receives track 428, so that stop member 438 and adjustable lock member 430 move together in a telescoping manner relative to track 428, which remains stationary relative to barrel 412. Track 428 includes a plurality of evenly-spaced teeth that are engaged by a tooth-engaging projection of the adjustable lock member 430, similar to the tracks and adjustable lock members described above. Syringe 410 includes a barrel flange 422 having a through-hole 440 for receiving stop member 438. Rather than being coupled to plunger 414, stop member 438 is coupled to adjustable lock member 430 so that stop member 438 moves with lock member 430 and moves through hole 440 of barrel flange 422 as lock member 430 is moved or repositioned along track 422, as shown with reference to FIGS. 10 and 11. It will be appreciated that, optionally, the track and adjustable lock member may be substantially identical to track 28 and adjustable lock member 30, described above, but with the stop member coupled to the adjustable lock member so that these components move together. Various other components of syringe 410 are substantially similar to components of syringe 10 and are given like numerals by the addition of 400, such that the components of syringe 410 may be understood with reference to the above discussion of syringe 10.

The desired dosage may be set with the dosage control syringe 410 by repositioning adjustable lock member 430 along track 428 while plunger 414 is at least partially extracted from barrel 412 (FIGS. 10 and 11). This in turn repositions stop member with its upper end spaced a distance from the underside of plunger flange 426 according to the desired dose (FIG. 11). When plunger 414 is urged downwardly along barrel 412 to expel fluid from fluid chamber 416, plunger 414 moves freely until plunger flange 426 contacts and is halted by stop member 438 (FIG. 12), which is fixed against downward movement by adjustable lock member 430 on track 428. Accordingly, syringe 410 functions in a similar manner as syringe 10, but with a stop member 438 that is coupled to adjustable lock member 430 and is contacted by the syringe flange 426 when the proper dose has been expelled from fluid chamber 416, rather than a stop member that is coupled to a syringe flange, and that contacts an adjustable lock member when the proper dose has been expelled.

Another dosage control syringe 510, is similar in some respects to syringe 410 described above, and includes a barrel 512 and plunger 514 (FIGS. 10-12). Unlike the syringe 410, however, syringe 510 has a stop member 538 with an upper stop portion 542 that extends laterally over a portion of a plunger flange 526. Upper stop portion 542 is engaged by plunger flange 526 when the plunger 514 has been withdrawn a distance corresponding to the pre-selected volume indicated by a pointer or indicator portion 531, which projects from an adjustable lock member 530 that is movably and selectively lockably disposed along track 528. When lock member 530 is released by the user, it is locked in position along a track 528, so that upper stop portion 542 limits the distance that plunger 514 can be withdrawn when plunger flange 526 engages stop portion 542.

Figure 13:
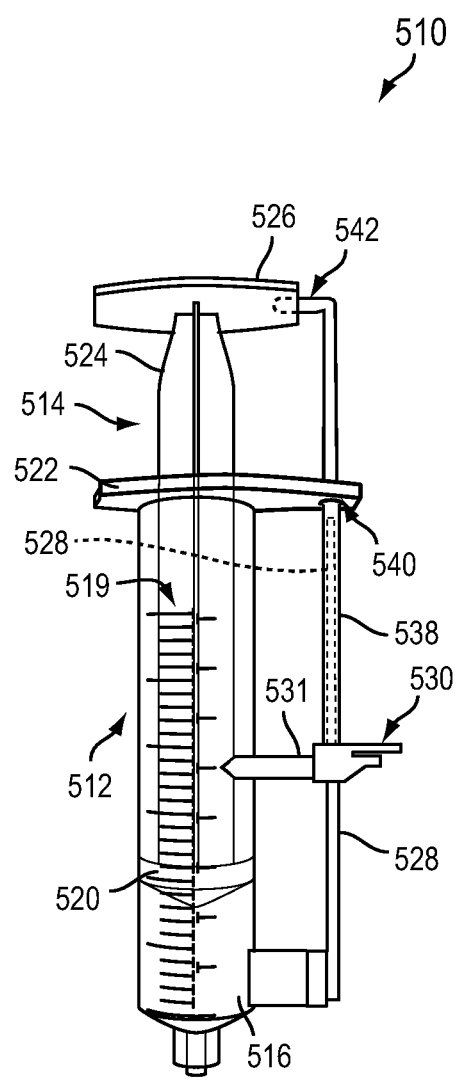
FIG. 13 is a side perspective view of another dosage control syringe in accordance with the present invention.

Track 528 and adjustable lock member 530 may be substantially similar or identical to track 428 and adjustable lock member 430 of syringe 410, described above, including a tubular stop member 538 having a hollow central portion that receives track 528. Barrel flange 522 projects further outwardly than the flange 422 of syringe 410, and defines a through-hole 540 for receiving stop member 538. Stop member 538 is coupled to adjustable lock member 530 so that stop member 538 moves with lock member 530 and moves through hole 540 of barrel flange 522 as lock member 530 is moved or repositioned along track 522, as shown with reference to FIG. 13. Prior to use of syringe 510, plunger 514 is typically inserted fully into barrel 512 so that plunger flange 526 is in close proximity to barrel flange 522, and stop member 538 (and lock member 530) may also be fully lowered or retracted so that upper stop portion 542 rests atop or adjacent plunger flange 526. Various other components of syringe 510 are substantially similar to components of syringe 10 and are given like numerals by the addition of 500, such that the components of syringe 510 may be understood with reference to the above discussion of syringe 10.

The desired dosage is typically set with the dosage control syringe 510 by repositioning adjustable lock member 530 along track 528 while plunger 514 is fully retracted into the barrel 512. This in turn repositions stop member 538 with its upper stop portion 542 spaced a distance outwardly beyond the upper surface of plunger flange 526, so that plunger 514 will stop once it has been withdrawn a distance that corresponds to a desired volume set by lock member, which draws a pre-selected volume of liquid into barrel 512. When plunger 514 is urged downwardly along barrel 512 to expel fluid from fluid chamber 516, plunger 514 moves freely until the entire volume of fluid has been expelled.

Accordingly, rather than dispensing only a predetermined portion of the contents of the syringe, dosage control syringe 510 is configured so that the entire contents is pre-measured by medical personnel (e.g. by drawing the liquid medication into barrel 512 from a vial). The entire pre-measured contents in barrel 512 may then be dispensed into the patient, as opposed to dispensing only a portion of a larger volume of liquid, as with the other syringes described above.

Thus, the present invention provides a dosage control syringe that can be pre-set according to a desired dosage by moving an adjustable lock member along a track, such as to align the lock member with indicia visible along the outer wall of the barrel, and then depressing a plunger whose travel is limited (during either a withdrawal stroke or an injection stroke) by the adjustable lock member. In some embodiments, any fluid remaining in the fluid chamber after the pre-set dosage has been expelled from the syringe can be reserved for use with the same patient or, more likely, can be discarded. In other embodiments, the fluid in the syringe is pre-measured according to the position of the lock member, so that the entire liquid volume will be dispensed. Once the adjustable lock member is set and the syringe is at least partially filled with fluid, the desired dose of fluid may be dispensed from the syringe without visual reference to the syringe. Thus, a syringe may be preset to a desired dosage for a patient well before the fluid in the syringe is needed for the patient, and administered without further reference to the syringe, to reduce the likelihood of dosing errors that may be more likely to occur during high workload and/or high stress medical situations.

Although primarily described with reference to syringes equipped with hypodermic needles for medical use, it will be appreciated that the present invention is applicable to other medical uses, such as irrigating wounds with cleansing or antibiotic fluids, or for administering oral medications. It will further be appreciated that non-medical applications are envisioned for the invention, including substantially any use or application in which it is desirable to dispense a measured quantity of fluid from a syringe or a syringe-like device, particularly when less than all of the fluid in the device is to be dispensed. Such applications may include, for example, use in chemical, biological, or medical laboratories.

Changes and modifications in the specifically described embodiments may be carried out without departing from the principles of the present invention, which is intended to be limited only by the scope of the appended claims, as interpreted according to the principles of patent law including the doctrine of equivalents.

The invention claimed is:

1. A syringe comprising:
a barrel defining a fluid chamber and having a longitudinal axis;
a plunger at least partially disposed in said fluid chamber of said barrel and having a sealing member for slidably and sealingly engaging said barrel, said plunger having a plunger flange extending outwardly away from the longitudinal axis and laterally outboard of said barrel;
an elongate guide disposed along said barrel;
an adjustable lock member movably disposed along said elongate guide;
a stop member coupled to one of said adjustable lock member and said plunger flange and aligned so as to selectively contact the other of said adjustable lock member and said plunger flange; and
wherein when said plunger is moved sufficiently so that said stop member contacts said other of said adjustable lock member and said plunger flange, further movement of said plunger relative to said barrel is substantially precluded.

2. The syringe of claim 1, wherein said lock member is configurable between a locking configuration in which said lock member lockably engages said elongate guide, and a movable configuration in which said lock member is movable along said elongate guide.

3. The syringe of claim 2, wherein said elongate guide comprises a track having plurality of ratchet teeth and said lock member comprises a tooth-engaging projection, said tooth-engaging projection being operable to selectively engage at least one of said ratchet teeth wherein said lock member lockably engages said track, and to selectively disengage said ratchet teeth wherein said lock member is movable along said track.

4. The syringe of claim 3, wherein said lock member comprises a trigger release operable to disengage said tooth-engaging projection from said ratchet teeth of said track.

5. The syringe of claim 3, wherein said plurality of ratchet teeth are evenly spaced from one another in a manner that corresponds to fixed-increment volumetric changes of said fluid chamber when said plunger is moved so that said stop member contacts said other of said adjustable lock member and said plunger flange.

6. The syringe of claim 3, wherein said stop member comprises a tubular member attached to said adjustable lock member, said tubular member receiving said track in a telescoping manner.

7. The syringe of claim 1, wherein said barrel comprises an outer surface and wherein said elongate guide is established along said outer surface.

8. The syringe of claim 1, wherein said barrel comprises a double-wall barrel having an outer wall spaced outwardly from an inner wall, said inner wall comprising an inner surface defining said fluid chamber, and said outer wall comprising an outer surface.

9. The syringe of claim 8, wherein said guide is established along said outer surface of said outer wall.

10. The syringe of claim 8, wherein said guide is established along an outer surface of said inner wall, and wherein said outer wall comprises a slot for receiving said guide and/or said adjustable lock member.

11. The syringe of claim 1, wherein said outer wall of said barrel comprises indicia indicative of dosage.

12. The syringe of claim 11, wherein said indicia are generally aligned with said elongate guide.

13. The syringe of claim 1, wherein said barrel comprises a barrel flange extending generally perpendicular to the longitudinal axis, said barrel flange comprising an opening for receiving said stop member of said plunger, and wherein said stop member moves through said opening of said barrel flange as said plunger travels along said barrel.

14. The syringe of claim 1, wherein said barrel comprises a barrel flange extending generally perpendicular to the longitudinal axis, said barrel flange comprising an opening for receiving said stop member of said plunger, and wherein said stop member moves through said opening of said barrel flange as said adjustable stop member moves along said elongate guide.

15. The syringe of claim 1, further comprising at least one chosen from a hypodermic needle and a nozzle in communication with said fluid chamber for directing a fluid out of said fluid chamber.

16. The syringe of claim 1, wherein said stop member is coupled to said adjustable lock member and is configured to be engaged by an upper surface of said plunger flange when said plunger is withdrawn a distance from said barrel corresponding to a preselected volume of said fluid chamber.

17. A syringe comprising:
a barrel having a longitudinal axis, an outer surface, and an inner surface, said inner surface defining a fluid chamber, said outer and inner surfaces spaced outwardly from the longitudinal axis;
a plunger having first and second opposed end portions, said first end portion disposed in said fluid chamber of said barrel and having a sealing member disposed at said first end portion, said sealing member slidably and sealingly engaging said inner surface of said barrel, said second end portion having a plunger flange, said plunger flange extending outwardly away from the longitudinal axis;
an elongate guide disposed outboard of said inner surface of said barrel and aligned generally parallel with the longitudinal axis;
an adjustable lock member movably disposed along said elongate guide;
a stop member disposed outboard of said outer surface of said barrel and aligned generally parallel with the longitudinal axis, said stop member coupled to one of said adjustable lock member and said plunger flange and aligned so as to selectively contact the other of said adjustable lock member and said plunger flange; and wherein when said plunger is moved sufficiently so that said stop member contacts said other of said adjustable lock member and said plunger flange, further movement of said plunger relative to said barrel is substantially precluded.

18. The syringe of claim 17, wherein said lock member is configurable between a locking configuration in which said lock member lockably engages said elongate guide, and a movable configuration in which said lock member is movable along said elongate guide.

19. The syringe of claim 18, wherein said elongate guide comprises a track having plurality of ratchet teeth and said lock member comprises a tooth-engaging projection, said tooth-engaging projection being operable to selectively engage at least one of said ratchet teeth wherein said lock member lockably engages said track, and to selectively disengage said ratchet teeth wherein said lock member is movable along said track.

20. The syringe of claim 19, wherein said lock member comprises a trigger release operable to disengage said tooth-engaging projection from said ratchet teeth of said track.

21. The syringe of claim 17, wherein said elongate guide is established along said outer surface of said barrel.

22. The syringe of claim 17, wherein said barrel comprises a double-wall barrel having an outer wall spaced outwardly from an inner wall, said inner wall comprising said inner surface defining said fluid chamber, and said outer wall comprising said outer surface.

23. The syringe of claim 22, wherein said guide is established along said outer surface of said outer wall.

24. The syringe of claim 22, wherein said guide is established along an outer surface of said inner wall, and wherein said outer wall comprises a slot for receiving said guide and/or said adjustable lock member.

25. The syringe of claim 17, wherein said outer wall of said barrel comprises indicia indicative of dosage.

26. The syringe of claim 25, wherein said indicia are generally aligned with said elongate guide.

27. The syringe of claim 25, wherein said lock member comprises an indicator that aligns with said indicia to indicate the dosage corresponding to the position of said lock member on said elongate guide.

28. The syringe of claim 17, wherein said barrel comprises a barrel flange extending generally perpendicular to the longitudinal axis, said barrel flange comprising an opening for receiving said stop member of said plunger, and wherein said stop member moves through said opening of said barrel flange as said plunger travels along said barrel.

29. The syringe of claim 28, wherein said barrel flange comprises a support tube defining said opening and supporting said stop member of said plunger to limit buckling or flexing of said stop member.

30. The syringe of claim 17, further comprising at least one chosen from a hypodermic needle and a nozzle in communication with said fluid chamber for directing a fluid out of said fluid chamber.

\* \* \* \* \*